United States Patent [19]

Johnson

[11] Patent Number: 5,533,499
[45] Date of Patent: Jul. 9, 1996

[54] NASAL DILATOR

[75] Inventor: Bruce C. Johnson, St. Paul, Minn.

[73] Assignee: Creative Integration & Design, Inc., St. Paul, Minn.

[21] Appl. No.: 183,916

[22] Filed: Jan. 19, 1994

Related U.S. Application Data

[63] Continuation of Ser. No. 48,589, Apr. 16, 1993, abandoned, which is a continuation of Ser. No. 884,626, May 15, 1992, abandoned, which is a continuation of Ser. No. 712,508, Jun. 10, 1991, abandoned.

[51] Int. Cl.$^6$ .............. A61F 5/08; A61M 29/00; A61M 15/08; A62B 7/00
[52] U.S. Cl. .............. 128/200.24; 606/199; 606/204.45
[58] Field of Search .................... 128/204.12, 207.18, 128/848, 858, 912, DIG. 26; 606/191, 196, 199, 204.45, 198; 602/5, 6, 12, 14, 16, 17, 46, 47, 61, 74

[56] References Cited

U.S. PATENT DOCUMENTS

| | | | |
|---|---|---|---|
| 850,978 | 4/1907 | Soares | 128/163 |
| 1,043,924 | 11/1912 | Gottlieb | 606/199 |
| 1,292,083 | 1/1919 | Sawyer | 606/199 |
| 1,950,839 | 3/1934 | Chirila | 606/199 |
| 2,001,862 | 5/1935 | Battey | 128/163 |
| 2,398,073 | 4/1946 | Bonde | 128/87 R |
| 2,509,157 | 5/1950 | Lind | 128/87 |
| 2,566,148 | 8/1951 | Sky | 128/117 |
| 2,586,219 | 2/1952 | Geffas | 122/117 |
| 2,625,931 | 1/1953 | Phillips | 128/104 |
| 3,046,989 | 7/1962 | Hill | 128/207.18 |
| 3,426,751 | 2/1969 | Radewan | 128/76 C |
| 3,531,090 | 9/1970 | Laible | 256/10 |
| 3,742,943 | 7/1973 | Malmin | 128/76 C |
| 3,835,848 | 9/1974 | Berner | 128/76 C |
| 3,935,859 | 2/1976 | Doyle | 128/89 |
| 4,153,051 | 5/1979 | Shippert | 128/89 |
| 4,213,452 | 7/1980 | Shippert | 128/89 |
| 4,274,402 | 6/1981 | Shippert | 128/89 |
| 4,340,040 | 7/1982 | Straith | 128/76 C |
| 4,402,314 | 9/1983 | Goode | 128/87 R |
| 4,414,977 | 11/1983 | Rezakhany | 128/342 |
| 4,534,342 | 8/1985 | Paxa | 182/163 |
| 4,674,133 | 6/1987 | Oschner | 2/206 |
| 4,823,789 | 4/1989 | Beisang, III | 128/207.18 |
| 4,932,943 | 6/1990 | Nowak | 604/180 |
| 4,971,282 | 11/1990 | Dickinson | 248/231.8 |
| 4,984,302 | 1/1991 | Lincoln | 2/206 |
| 4,995,114 | 2/1991 | Price, Jr. | 2/15 |
| 5,003,971 | 4/1991 | Buckley | 128/156 |
| 5,022,389 | 6/1991 | Brennan | 128/858 |
| 5,101,837 | 4/1992 | Perrin | 128/888 |

FOREIGN PATENT DOCUMENTS

| | | | |
|---|---|---|---|
| 437661 | 11/1926 | Germany | 128/76 C |
| 00043006 | 3/1928 | Germany | 606/204.45 |
| 12987 | of 1899 | United Kingdom | 128/76 C |

OTHER PUBLICATIONS

CoNco Article "Nasal Splint", p. 12, Oct. 10, 172.

*Primary Examiner*—Kimberly L. Asher
*Attorney, Agent, or Firm*—Kinney & Lange

[57] ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing.

32 Claims, 3 Drawing Sheets

NASAL DILATOR

This is a continuation of the application having Ser. No. 08/048,589, filed on Apr. 16, 1993, now abandoned which was a continuation of the application having Ser. No. 07/884,626, filed on May 15, 1992, now abandoned which was a continuation of the application having Ser. No. 07/712,508, filed on Jun. 10, 1991, now abandoned.

BACKGROUND OF THE INVENTION

This invention relates generally to the field of devices for the treatment of malformations. In particular, the present invention is a nasal dilator for preventing outerwall tissue of nasal passages of a nose from drawing in during breathing.

A portion of the human population has some malformation of the nasal passages which makes breathing difficult. Example of such malformations are a deviated septum and swelling due to allergic reactions. The lower portion of the nostril, immediately above the entrance to the nostril, is known as a vestibule. The vestibule tapers inwardly to a narrowed neck-like area called the ostium internum. Above the ostium internum the nasal passages widen out again. Nasal obstructions commonly occur at the ostium in individuals who have swelling due to allergic reactions, a deviated septum or similar condition, to the point that the ostium may be substantially blocked. Commonly, the lateral wall (i.e., the outer wall tissue of the nasal passage) at the ostium is loose with the result that the outer wall tissue draws in during the process of inhalation to substantially block the passage of air through the nasal passage. The drawing in of the outer wall tissue act as a "check valve" to block air flow during in-breathing.

Blockage of the nasal passages is obviously an inconvenience to persons who experience it. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is uncomfortable for many people who have such a problem to breathe through the mouth while asleep. Nasal blockage can lead to sleep disturbances and irregularities, since a person with such a condition may wake often because he/she is not inhaling sufficient quantities of oxygen.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose are generally known. U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the ostium within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective since they are uncomfortable to wear. Because the nasal dilators must be inserted within the nasal passages they may cause irritation and itching. In addition, these nasal dilators must be custom-made to fit each nasal passage of an individual.

It is evident that there is a continuing need for improved nasal dilators for preventing outer wall tissue of nasal passages of a nose from drawing in during breathing. Specifically, there is a need for a nasal dilator that can provide effective relief without the need of inserting an object within the nasal passage. Moreover, there is a need for a nasal dilator that can be worn at night when the nasal blockage problem is most acute and most uncomfortable. The nasal dilator should be of efficient design and relatively uncomplicated and provide effective stabilization of the outer wall tissue of the nasal passages to provide effective relief from nasal blockage during inhalation. In addition, the nasal dilator should provide this effective stabilization without undue discomfort to the wearer.

SUMMARY OF THE INVENTION

The present invention is a nasal dilator for preventing outer wall tissue of nasal passages of a nose from drawing in during breathing. The nasal dilator comprises a truss member having a first end region adapted to engage the outer wall tissue of a first nasal passage. A second end region of the truss member is configured to engage the outer wall tissue of a second nasal passage. The first and second end regions of the truss member are coupled to one another by an intermediate segment. The intermediate segment is configured to traverse a portion of the nose located between the first and second nasal passages. The truss member, when in place, acts to stabilize the outer wall tissue and thereby prevent the outer wall tissue of the first and second nasal passages from drawing in during breathing.

The truss member includes a flexible strip of material that defines the first and second end regions and the intermediate segment of nasal dilator. A first resilient band is secured to a first side of the strip of material adjacent a first edge of the material. A second resilient band spaced from the first resilient band is secured to the first side of the strip of material adjacent a second edge thereof. The first and second resilient bands are oriented generally parallel to one another and substantially parallel to the longitudinal extent of the strip of material.

Each of the first and second resilient bands includes a plurality of grooves that extend substantially parallel to the respective resilient band. The grooves create areas of reduced material to enhance the flexibility of the first and second resilient bands in a direction perpendicular to the grooves. In addition, each of the first and second resilient bands includes first and second angled ends. The first and second angled ends extend towards the first side of the strip of material and help to prevent the first and second resilient bands from readily separating from the strip of material when the truss member is flexed. The resiliency of the first and second resilient bands prevent the outer wall tissue of the first and second nasal passages from drawing in during breathing.

The truss member further includes an adhesive substance located on a second side of the flexible strip of material. The adhesive substance acts to releasably secure the truss member to the outer wall tissue of the first and second nasal passages. First and second release liners cover the adhesive substance on the first and second end regions. The first and second release liners are readily removable from the strip of material to expose the adhesive substance and permit the truss member to be secured to the outer wall tissue of the first and second nasal passages.

This nasal dilator is of efficient design and effectively prevents the outer wall tissue of the first and second nasal passages of the nose from drawing in during breathing. In addition, the nasal dilator provides effective relief of nasal blockage during inhalation without the irritation and discomfort normally associated with nasal dilators that are inserted within the nasal passages. Moreover, this nasal dilator can be worn at night when the inhalation nasal blockage problem is most acute, without the anxiety and inconvenience normally associated with custom made, internally worn nasal dilators.

DETAILED DESCRIPTION OF THE PREFERRED EMBODIMENTS

Figure 1:
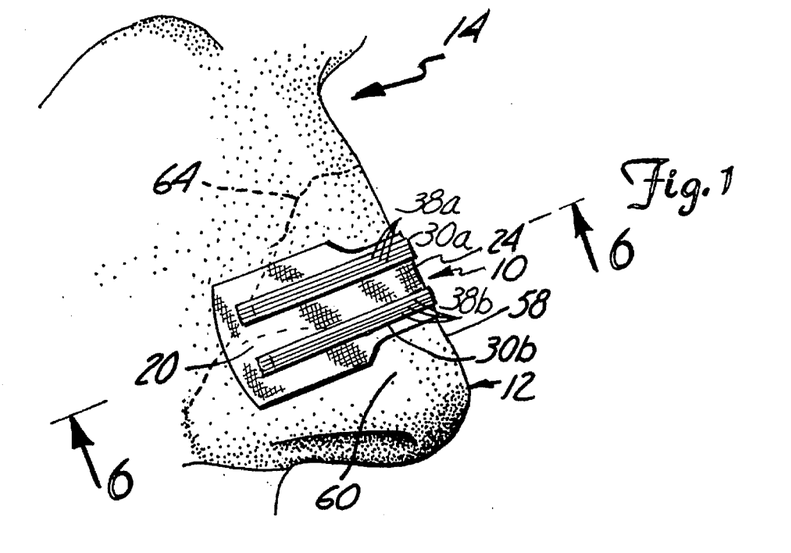
FIG. 1 is perspective view of a portion of a face with a nasal dilator in accordance with the present invention secured to a nose.

A nasal dilator 10 in accordance with the present invention is illustrated generally in FIG. 1. The nasal dilator 10 is shown secured to a nose 12 of a wearer 14.

Figure 2:
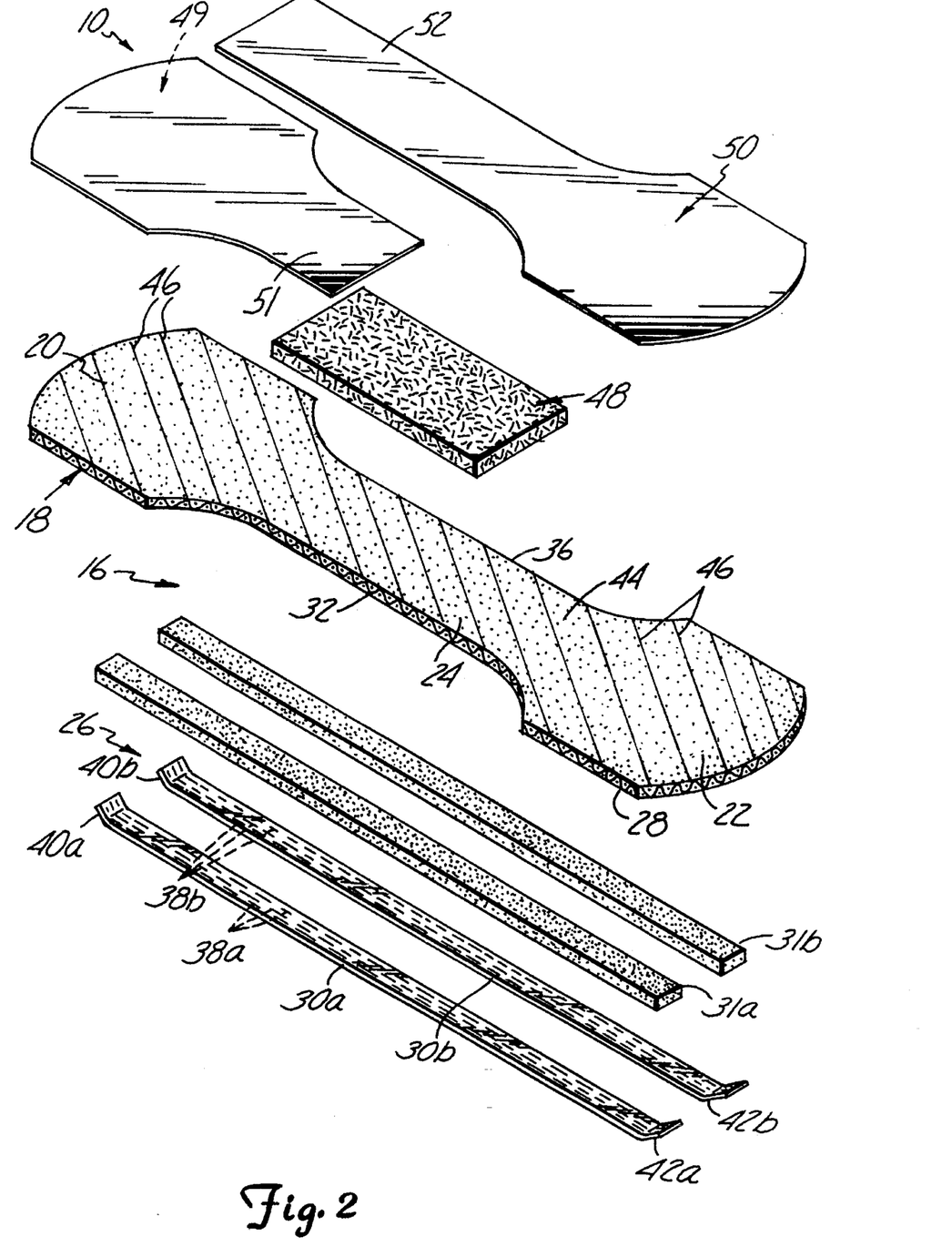
FIG. 2 is an exploded perspective view showing the components of the nasal dilator in accordance with the present invention.

As seen in FIG. 2, the nasal dilator 10 comprises a truss member 16 including a flexible strip of material 18 having a first end region 20 and a second end region 22 coupled to the first end region 20 by way of an intermediate segment 24. The width of the intermediate segment 24 is less than the width of the first and second end regions 20 and 22. The flexible strip of material 18 is preferably formed of an interwoven piece of fabric that allows the skin of the nose 12 to breathe to maximize comfort and minimize irritation. As an alternative, the strip of material 18 may be formed of a plastic film.

The truss member further includes resilient means 26 secured to a first side 28 of the strip of material 18. The resilient means 26 includes a first resilient band 30a secured by a first adhesive member 31a to the first side 28 of the strip of material 18. The first resilient band 30a is secured to the strip of material 18 adjacent a first edge 32 of the intermediate segment 24. In addition, a second resilient band 30b, spaced from the first resilient band 30a, is secured by a second adhesive member 31b to the first side 28 of the strip of material 18. The second resilient band 30b is secured to the strip of material 18 adjacent a second edge 36 of the intermediate segment 24. The first and second resilient bands 30a and 30b are oriented generally parallel to one another and substantially parallel to the longitudinal extent of the flexible strip of material 18. Each of the first and second adhesive members 31a and 31b is formed of an adhesive material such as double sided adhesive, foam tape.

Each of the first and second resilient bands 30a and 30b includes a plurality of grooves 38a and 38b, respectively, that extend substantially parallel to the respective resilient band 30a and 30b. As seen best in FIG. 2, the grooves 38a and 38b are formed in the exposed sides of the first and second resilient bands 30a and 30b (i.e., the sides of the first and second resilient bands 30a and 30b opposite that to which the first and second adhesive members 31a and 31b are secured). The grooves 38a and 38b create areas of reduced material to enhance the flexibility of the first and second resilient bands 30a and 30b in a direction perpendicular to the plurality of grooves 38a and 38b. In addition, each of the first and second resilient bands 30a and 30b includes first angled ends 40a and 40b, respectively, and second angled ends 42a and 42b, respectively. The first and second angled ends 40a, b and 42a, b extend towards the first side 28 of the strip of material 18 and help to prevent the first and second resilient bands 30a and 30b from readily separating from the strip of material 18 and the first and second adhesive members 31a and 31b when the truss member 10 is flexed. The first and second resilient bands 30a and 30b are formed of a plastic material.

As seen in FIG. 2, a second side 44 of the strip of material 18 includes a layer of an adhesive substance 46 that extends over the first and second end regions 20 and 22 and the intermediate segment 24. The adhesive substance 46 is bio-compatible with the skin of the nose 12. A padded element 48 is secured to the median of the intermediate segment 24 via the adhesive substance 46. Readily removable, first and second release liners 49 and 50, respectively, cover the adhesive substance 46 on the first and second end regions 20 and 22, respectively, of the strip of material 18. The first and second release liners 49 and 50 cover the adhesive substance 46 and remain in place on the strip of material 18 until the nasal dilator 10 is to be used. The first and second release liners 49 and 50 also include extensions 51 and 52, respectively, that cover the padded element 48 and further act to protect the padded element 48 until the nasal dilator 10 is to be secured to the nose 12 of a wearer 14.

Figure 3:
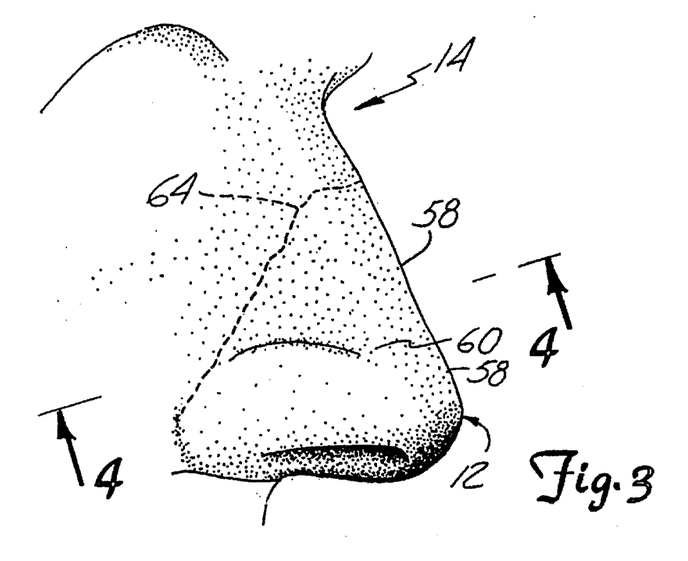
FIG. 3 is a perspective view similar to FIG. 1 with the nasal dilator in accordance with the present invention removed from the nose.
Figure 4:
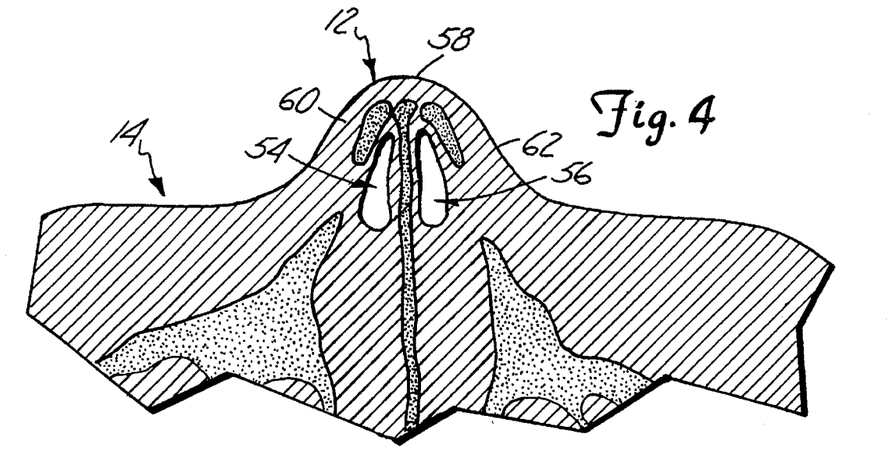
FIG. 4 is a sectional view taken along line 4—4 in FIG. 3 showing the nose in a state wherein no appreciable flow of air is occurring in the nasal passages.
Figure 5:
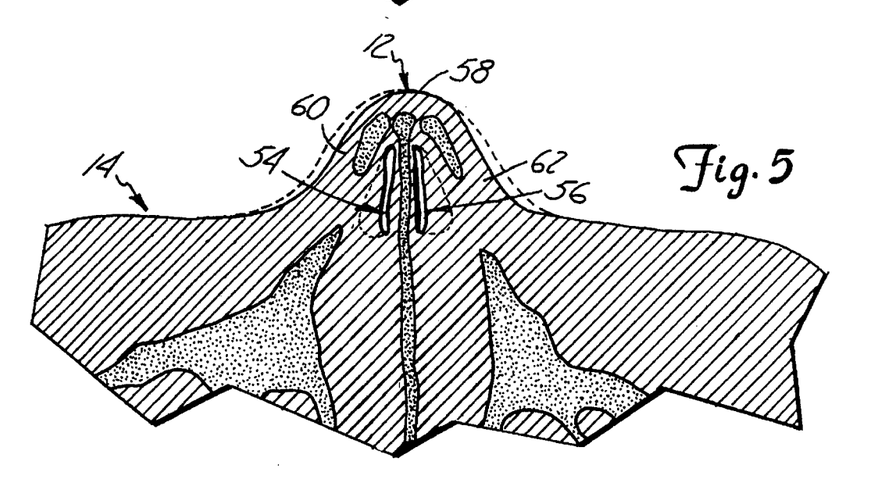
FIG. 5 is a sectional view similar to FIG. 4 showing the state of the nose during inhalation.

As seen in FIGS. 3 and 4, the nose 12 includes a first nasal passage 54, a second nasal passages 56 and a portion of the nose 12 known as the bridge 58 located between the first and second nasal passages 54 and 56. FIG. 4 shows the state of the first and second nasal passages 54 and 56 when no appreciable flow of air is occurring through the nasal passages 54 and 56. Due to a malformation, such as a deviated septum or swelling due to allergic reactions, outer wall tissue 60 and 62 of the first and second nasal passages 54 and 56, respectively, tends to be drawn in (i.e., collapse) during inhalation (see FIG. 5). This drawing in during inhalation is caused by reduced air pressure within the first and second nasal passages 54 and 56 as a result of an increase in air velocity as the in drawn breath travels through the first and second nasal passages 54 and 56. The portion (i.e., the ostium) of the outer wall tissue 60 and 62 drawn in during inhalation is that located between the nasal cartilage 64 (shown in dashed lines in FIGS. 1 and 3) and the entrance to the nasal passages 54 and 56. This drawing in of the outer wall tissue 60 and 62 causes nasal blockage. The nasal dilator 10 of the present invention remedies this problem.

Figure 6:
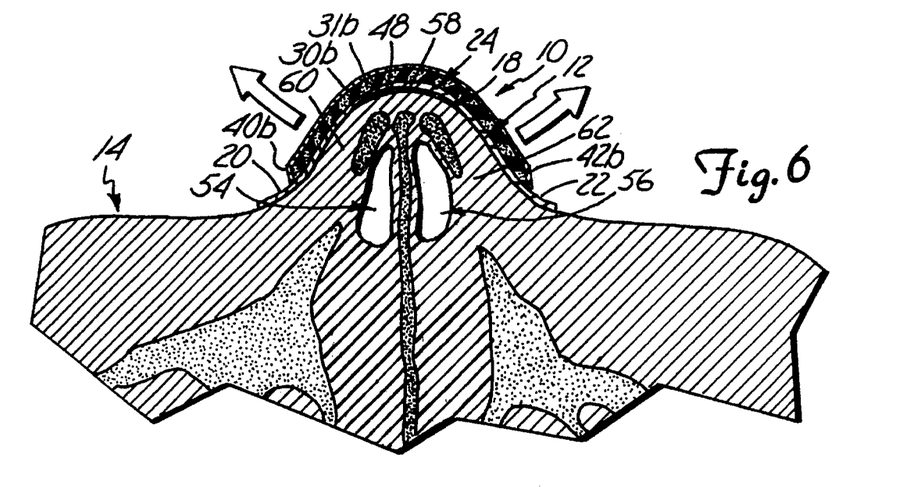
FIG. 6 is a sectional view taken along line 6—6 in FIG. 1 showing the state of the nose during inhalation with the nasal dilator in accordance with the present invention secured thereto.

To secure the nasal dilator 10 to the nose 12, the first and second release liners 49 and 50 are removed from the flexible strip of material 18 to expose the adhesive substance 46. As seen in FIGS. 1 and 6, the nasal dilator 10 is placed on the exterior of the nose 12 such that the intermediate segment 24 traverses the bridge 58 of the nose 12 and the first and second end regions 20 and 22 contact the outer wall tissue 60 and 62 of the first and second nasal passages 54 and 56. The adhesive substance 46 on the first and second end regions 20 and 22 releasably secures the truss member 16 to the outer wall tissue 60 and 62 of the first and second nasal passages 54 and 56. As seen in FIG. 6, the padded element 48 creates an absorbent adhesive void between the truss member 16 and the bridge 58. This absorbent adhesive void absorbs moisture due to perspiration or the like. With the nasal dilator 10 in place about the nose 12, the resiliency of the first and second resilient bands 30a and 30b (i.e., the tendency of the resilient bands to return to their normally planar state shown in FIG. 2) acts to stabilize the outer wall tissue 60 and 62 and thereby prevents the outer wall tissue 60 and 62 of the first and second nasal passages 54 and 56 from drawing in during breathing (i.e., during inhalation). In addition, the flexibility of the strip of material 18 and the first and second adhesive members 31a and 31b, the resiliency of the first and second bands 30a and 30b, and the flexibility of the first and second bands 30a and 30b due to the grooves 38a and 38b, all allow the nasal dilator 10 to closely conform to the curves of the nose of each individual wearer.

This nasal dilator 10 is of efficient design and effectively prevents the outer wall tissue 60 and 62 of the first and second nasal passages 54 and 56 of the nose 12 from drawing in during breathing. In addition, the nasal dilator 10 provides effective relief of nasal blockage during .inhalation without the irritation and discomfort normally associated with nasal dilators that are inserted within the nasal passages. Moreover, this nasal dilator 10 can be worn at night when the inhalation nasal blockage problem is most acute, without the anxiety and inconvenience normally associated with custom made, internally worn nasal dilators.

Although the present invention has been described with reference to preferred embodiments, workers skilled in the art will recognize that changes may be made in form and detail without departing from the spirit and scope of the invention.

What is claimed is:

1. A nasal dilator for preventing outer wall tissue of nasal passages of a nose from drawing in during breathing, comprising:

a unitary truss member having a normally, substantially planar state, the unitary truss member including:
a first end region adapted to engage the outer wall tissue of a first nasal passage;
a second end region adapted to engage the outer wall tissue of a second nasal passage;
an intermediate segment configured to traverse a portion of a nose located between the first and second nasal passages, the inherent tendency of the truss member to return to its normally planar state when flexed acting to stabilize the outer wall tissue and thereby prevent the outer wall tissue of the first and second nasal passages from drawing in during breathing;
a resilient member secured to at least a portion of the first and second end regions and the intermediate segment, the resilient member being capable, at least in part, of deformation that allows the truss member to conform to the outer wall tissue of the nasal passages of a nose.

2. The nasal dilator of claim 1 wherein the truss member includes:

a flexible strip of material defining the first and second end regions and the intermediate segment; and
said resilient member secured to a first side of the flexible strip of material by way of a deformable means, the resilient member defining the normally planar state of the truss member.

3. The nasal dilator of claim 2, and further including:

an adhesive substance located on a second side of the flexible strip of material at the first and second end regions thereof for releasably securing the truss member to the outer wall tissue of the first and second nasal passages.

4. The nasal dilator of claim 3, and further including:

first and second release liners covering the adhesive substance on the first and second end regions, respectively, of the flexible strip of material, the first and second release liners being readily removable from the flexible strip of material to expose the adhesive substance and permit the truss member to be secured to the outer wall tissue of the first and second nasal passages.

5. The nasal dilator of claim 2 wherein the flexible strip of material is formed of an interwoven piece of fabric.

6. The nasal dilator of claim 2 wherein the resilient member includes:

at least one resilient band oriented substantially parallel to a longitudinal extent of the flexible strip of material, the resiliency of the at least one resilient band acting to prevent the outer wall tissue of the first and second nasal passages from drawing in during breathing.

7. The nasal dilator of claim 1 wherein the intermediate segment of the truss member includes an adhesive void, and wherein the truss member is configured to extend about a nose such that the intermediate segment traverses an exterior region of a bridge of a nose with the adhesive void located between the truss member and the bridge, the first end region engaging an exterior surface of the outer wall tissue of the first nasal passage and the second end region engaging an exterior surface of the outer wall tissue of the second nasal passage.

8. The nasal dilator of claim 1 wherein the resilient member stabilizes the outer wall tissue by dilating the first and second nasal passages to thereby prevent the outer wall tissue of the first and second nasal passages from drawing in during breathing.

9. The nasal dilator of claim 1 wherein the truss member is formed of a material that allows the skin of a nose to breathe to maximize comfort and minimize irritation.

10. A nasal dilator for preventing outer wall tissue of nasal passages of the nose from drawing in during breathing, comprising:

a unitary truss member having a normally, substantially planar state, the unitary truss member including:
a first end region adapted to engage the outer wall tissue of a first nasal passage;
a second end region adapted to engage the outer wall tissue of a second nasal passage;
an intermediate segment configured to traverse a portion of a nose located between the first and second nasal passages;
a flexible strip of material defining the first and second end regions and the intermediate segment;
a first resilient band secured to a first side of the flexible strip of material adjacent a first edge thereof;
a second resilient band secured to the first side of the flexible strip of material at a second edge thereof, the second resilient band being spaced from and extending generally parallel to the first resilient band; and a deformable means for allowing the truss member to conform to the outer wall tissue of the nasal passages of a nose through the deformable means capability of being deformable, said deformable means positioned in at least portions of the first and second end regions and the intermediate segment to secure said first and second resilient bands to said first side of said flexible strip, the first and second resilient bands defining a normally planar state of the truss member such that the inherent tendency of the truss member to return to this normally planar state when flexed acts to stabilize the outer wall tissue and thereby prevent the outer wall tissue of the first and second nasal passages from drawing in during breathing.

11. The nasal dilator of claim 10 wherein the deformable means is defined by first and second adhesive members that are configured to secure the first and second resilient bands, respectively, to the first side of the flexible strip of material, with each of the first and second adhesive members being formed of double sided adhesive, foam tape.

12. The nasal dilator of claim 10 wherein each of the first and second resilient bands includes a plurality of grooves that extend substantially parallel to a longitudinal extent of the respective resilient band, the grooves creating areas of reduced material to enhance the flexibility of the first and second resilient bands in a direction perpendicular to the plurality of grooves.

13. The nasal dilator of claim 12 wherein the first and second resilient bands are secured to the first side of the flexible strip of material by way of first and second adhesive members, respectively, which define the deformable means, each of the first and second resilient bands including a first surface and a second surface, and wherein the plurality of grooves are formed in the first surface of each of the first and second resilient bands, and the first and second adhesive members are secured to the second surfaces of the first and second resilient bands, respectively.

14. The nasal dilator of claim 10 wherein each of the first and second resilient bands includes first and second angled ends, the angled ends extending towards the first side of the flexible strip of material to help prevent the first and second resilient bands from readily separating from the flexible strip of material when the truss member is flexed.

15. The nasal dilator of claim 10 wherein the first and second resilient bands are formed of plastic.

16. A nasal dilator for preventing outer wall tissue of nasal passages of a nose from collapsing when inhaling, comprising:

a resilient, flexible truss member having a normally planar state, including:
  a first end region adapted to engage the outer wall tissue of a first nasal passage;
  a second end region adapted to engage the outer wall tissue of a second nasal passage;
  an intermediate segment, the truss member being unitary from the first end region to the second end region with the intermediate segment being configured to traverse an exterior region of a bridge of a nose located between the first and second nasal passages, the inherent tendency of the truss member to return to its normally planar state when flexed acting to stabilize the outer wall tissue and thereby prevent the outer wall tissue of the first and second nasal passages from collapsing when inhaling; and
  a deformable means secured in at least a portion of the first and second end regions and the intermediate segment for enhancing the flexibility of the truss member in a direction substantially perpendicular to a longitudinal extent of the truss member.

17. A nasal dilator for preventing outer wall tissue of nasal passages of a nose from drawing in during breathing, comprising:

a unitary truss member having a normally, substantially planar state, the unitary truss member including:
  a first end region engaging with an adhesive substance therein an exterior outer surface of the outer wall tissue of a first nasal passage;
  a second end region engaging with an adhesive substance therein an exterior surface of the outer wall tissue of a second nasal passage;
  an intermediate segment configured to traverse a portion of a nose located between the first and second nasal passages by extending about an exterior region of the bridge of that nose with there being an adhesive void located between the truss member and that exterior region of the bridge of a user's nose as provided by by an absorbent element, the inherent tendency of the truss member to return to its normally planar state when flexed acting to stabilize the outer wall tissue and thereby prevent the outer wall tissue of the first and second nasal passages from drawing in during breathing; and
  a deformable means for allowing the truss member to conform to the outer wall tissue of the nasal passages of a nose through the deformable means capability of being deformable, the deformable means defining at least a portion of the first and second end regions and the intermediate segment.

18. A nasal dilator capable of introducing separating stresses in nasal outer wall tissues, comprising:

a truss of a single body with a resilient member secured therein having a pair of spaced apart end surfaces which, if forced toward one another from initial positions to substantially reduce direct spacing therebetween by a spacing reduction force external to said truss, results in restoring forces in said truss tending to restore said direct spacing between said end surfaces; and engagement means adhered to said end surfaces and capable of engaging exposed surfaces of nasal outer wall tissues sufficiently to remain so engaged against said restoring forces.

19. The nasal dilator of claim 18 wherein said nasal dilator is configured to restrain nasal outer wall tissues adjacent nasal passages therein from being drawn in during breathing, said truss having sufficient restoring forces to substantially maintain during inhalation that spacing occurring between said end surfaces prior to inhalation.

20. The nasal dilator of claim 19 wherein said end surfaces are limited in separation therebetween so that, when said end surfaces are engaging nasal outer wall tissues adjacent nasal passages therein, a surface of said truss can be in contact with said nose for substantially all of that extent thereof between said end surfaces.

21. The nasal dilator of claim 18 wherein said truss includes deformable material between exposed surfaces of any nasal outer wall tissues engaged by said engagement means and said resilient member.

22. The nasal dilator of claim 21 wherein said single body of said truss further includes a flexible strip of said deformable material defining said pair of spaced apart end surfaces with said resilient member being secured to a first side of said flexible strip of deformable material.

23. The nasal dilator of claim 18 wherein said truss and said engagement means are capable of being manually released from exposed surfaces of any nasal outer wall tissues engaged by said engagement means.

24. The nasal dilator of claim 23 wherein said engagement means is an adhesive substance located on each of said pair of spaced apart end surfaces and capable of adhering to exposed surfaces of nasal outer wall tissues while adhering to said truss and yet permitting said truss and said engagement means to be manually released from exposed surfaces of any nasal outer wall tissues adhered to by said engagement means.

25. The nasal dilator of claim 24 wherein said adhesive substance located on each of said pair of spaced apart surfaces is capable of adhering to a covering means while adhering to said truss prior to any engaging of exposed surfaces of nasal wall tissues yet permitting said covering means to be manually removed therefrom.

26. The nasal dilator of claim 18 wherein said truss and said engagement means together are formed as a strip having a length substantially greater than either of its width and thickness, and a width substantially greater than its thickness everywhere along said length.

27. The nasal dilator of claim 26 wherein said strip is of substantially constant thickness.

28. The nasal dilator of claim 26 wherein said strip is substantially planar absent external forces applied thereto.

29. The nasal dilator of claim 18 wherein said restoring forces in said truss arising if said end surfaces are forced adjacent to one another by said spacing reduction forces are sufficient, upon removal of said spacing reduction forces, to restore most of said direct spacing present between said end surfaces before application of such spacing reduction forces.

30. The nasal dilator of claim 29 wherein said single body of said truss is of plastic construction.

31. The nasal dilator of claim 18 wherein said spaced-apart end surfaces of said truss are terminated by end edges at opposite ends of said truss, and wherein said resilient member provides said restoring forces in said truss tending to restore said spacing between end surfaces thereof, said resilient member having opposite ends thereof each ending short of said end edges.

32. The nasal dilator of claim 31 wherein said single body of said truss further includes a flexible strip of material defining said pair of spaced-apart end surfaces with said resilient member being deformably secured to a first side of said flexible strip of material.

* * * * *

UNITED STATES PATENT AND TRADEMARK OFFICE
CERTIFICATE OF CORRECTION

PATENT NO. : 5,533,499
DATED : JULY 9, 1996
INVENTOR(S) : BRUCE C. JOHNSON

It is certified that error appears in the above-indentified patent and that said Letters Patent is hereby corrected as shown below:

Col. 5, line 31, after "during", delete "."

Signed and Sealed this

Thirty-first Day of December, 1996

*Attest:*

BRUCE LEHMAN

*Attesting Officer*  *Commissioner of Patents and Trademarks*

(12) EX PARTE REEXAMINATION CERTIFICATE (6525th)
United States Patent
Johnson (10) Number: US 5,533,499 C1
(45) Certificate Issued: Nov. 18, 2008

(54) NASAL DILATOR

(75) Inventor: Bruce C. Johnson, St. Paul, MN (US)

(73) Assignee: Creative Integration & Design, Inc., St. Paul, MN (US)

Reexamination Request:
No. 90/005,509, Oct. 4, 1999

Reexamination Certificate for:
Patent No.: 5,533,499
Issued: Jul. 9, 1996
Appl. No.: 08/183,916
Filed: Jan. 19, 1994

Certificate of Correction issued Dec. 31, 1996.

Related U.S. Application Data (63) Continuation of application No. 08/048,589, filed on Apr. 16, 1993, now abandoned, which is a continuation of application No. 07/884,626, filed on May 15, 1992, now abandoned, which is a continuation of application No. 07/712,508, filed on Jun. 10, 1991, now abandoned.

(51) Int. Cl.
*A61M 29/00* (2006.01)
*A61M 15/08* (2006.01)
*A61F 5/56* (2006.01)
*A61F 5/08* (2006.01)
*A62B 7/00* (2006.01)

(52) U.S. Cl. ............... 128/200.24; 606/204.45; 606/199; 128/848; D24/135

(58) Field of Classification Search .............. None
See application file for complete search history.

(56) References Cited

U.S. PATENT DOCUMENTS

| | | | | |
|---|---|---|---|---|
| 2,399,545 A | * | 4/1946 | Davis | 602/47 |
| 2,633,128 A | * | 3/1953 | Schaefer | 602/42 |
| 3,885,559 A | * | 5/1975 | Economou | 602/47 |
| 3,900,027 A | * | 8/1975 | Keedwell | 602/55 |
| 4,212,296 A | * | 7/1980 | Schaar | 602/55 |
| RE35,408 E | | 12/1996 | Petruson | |

FOREIGN PATENT DOCUMENTS

ES 289561 * 10/1985

* cited by examiner

*Primary Examiner*—Glenn K Dawson (57) ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claim 17 is confirmed.

Claims 1, 18 and 21 are cancelled.

Claims 2, 7–10, 16, 19, 20, 22–23, 26, 29 and 31 are determined to be patentable as amended.

Claims 3–6, 11–15, 24, 25, 27, 28, 30 and 32, dependent on an amended claim, are determined to be patentable.

New claims 33–50 are added and determined to be patentable.

2. [The nasal dilator of claim 1 wherein the truss member includes:] *A nasal dilator for preventing outer wall tissue of nasal passages of a nose from drawing in during breathing, comprising:*
   *a unitary truss member having an initial state, the unitary truss member including:*
      *a first end region adapted to engage the outer wall tissue of a first nasal passage;*
      *a second end region adapted to engage the outer wall tissue of a second nasal passage;*
      *an intermediate segment configured to traverse a portion of a nose located between the first and second nasal passages, the inherent tendency of the truss member to return to its initial state when flexed acting to stabilize the outer wall tissue and thereby prevent the outer wall tissue of the first and second nasal passages from drawing in during breathing;*
      *a resilient member secured to at least a tissue engaging portion of each of the first and second end regions, which tissue engaging portions are adapted to directly engage such outer wall tissue, and to a portion of the intermediate segment, the resilient member being capable, at least in part, of deformation that allows the truss member to conform to the outer wall tissue of the nasal passages of a nose; and*
      a flexible strip of material defining the first and second end regions and the intermediate segment[; and] *wherein* said resilient member *is* secured to a first side of the flexible strip of material by way of a deformable means, the resilient member defining the [normally planar] *initial* state of the truss member.

7. The nasal dilator of claim [1] *2* wherein the intermediate segment of the truss member includes an adhesive void, and wherein the truss member is configured to extend about a nose such that the intermediate segment traverses an exterior region of a bridge of a nose with the adhesive void located between the truss member and the bridge, the first end region engaging an exterior surface of the outer wall tissue of the first nasal passage and the second end region engaging an exterior surface of the outer wall tissue of the second nasal passage.

8. The nasal dilator of claim [1] *2* wherein the resilient member stabilizes the outer wall tissue by dilating the first and second nasal passages to thereby prevent the outer wall tissue of the first and second nasal passages from drawing in during breathing.

9. The nasal dilator of claim [1] *2* wherein the truss member is formed of a material that allows the skin of a nose to breathe to maximize comfort and minimize irritation.

10. A nasal dilator for preventing outer wall tissue of nasal passages of the nose from drawing in during breathing, comprising:
   a unitary truss member having [a normally, substantially planar] *an initial* state, the unitary truss member including:
      a first end region adapted to engage the outer wall tissue of a first nasal passage;
      a second end region adapted to engage the outer wall tissue of a second nasal passage;
      an intermediate segment configured to traverse a portion of a nose located between the first and second nasal passages;
      a flexible strip of material defining the first and second end regions and the intermediate segment;
   a first resilient band secured to a first side of the flexible strip of material adjacent a first edge thereof;
   a second resilient band secured to the first side of the flexible strip of material at a second edge thereof, the second resilient band being spaced from and extending generally parallel to the first resilient band; and
   a deformable means for allowing the truss member to conform to the outer wall tissue of the nasal passages of a nose through the deformable means capability of being deformable, said deformable means positioned in at least portions of the first and second end regions and the intermediate segment to secure said first and second resilient bands to said first side of said flexible strip, the first and second resilient bands defining [a normally planar] *the initial* state of the truss member such that the inherent tendency of the truss member to return to this [normally planar] *initial* state when flexed acts to stabilize the outer wall tissue and thereby prevent the outer wall tissue of the first and second nasal passages from drawing in during breathing.

16. A nasal dilator for preventing outer wall tissue of nasal passages of a nose from collapsing when inhaling, comprising:
   a resilient, flexible truss member having [a normally planar] *an initial* state, including:
      a first end region adapted to engage the outer wall tissue of a first nasal passage;
      a second end region adapted to engage the outer wall tissue of a second nasal passage;
      an intermediate segment, the truss member being unitary from the first end region to the second end region with the intermediate segment being configured to traverse an exterior region of a bridge of a nose located between the first and second nasal passages, the inherent tendency of the truss member to return to its [normally planar] *initial* state when flexed acting to stabilize the outer wall tissue and thereby prevent the outer wall tissue of the first and second nasal passages from collapsing when inhaling; and
      a deformable means secured in at least a portion of the first and second end regions and the intermediate segment for enhancing the flexibility of the truss member in a direction substantially perpendicular to a longitudinal extent of the truss member.

19. The nasal dilator of claim [18] *23* wherein said nasal dilator is configured to restrain nasal outer wall tissues adjacent nasal passages therein from being drawn in during breathing, said truss having sufficient restoring forces to substantially maintain during inhalation that spacing occurring between said end surfaces prior to inhalation.

20. The nasal dilator of claim 19 wherein said end surfaces are limited in separation therebetween so that, when said end surfaces are engaging nasal outer wall tissues adjacent nasal passages [therein], a surface of said truss can be in contact with said nose for substantially all of that extent thereof between said end surfaces.

22. The nasal dilator of claim [21] *23* wherein said single body of said truss further includes a flexible strip of said deformable material defining said pair of spaced apart end surfaces with said resilient member being secured to a first side of said flexible strip of deformable material.

23. [The nasal dilator of claim 18 wherein] *A nasal dilator capable of introducing separating stresses in nasal outer wall tissues, comprising:*

*a truss of a single body with a resilient member secured therein having a pair of spaced apart end surfaces which, if forced toward one another from initial positions to substantially reduce direct spacing therebetween by a spacing reduction force external to said truss, results in restoring forces in said truss tending to restore said direct spacing between said end surfaces,* said truss being formed as a strip having a length greater than those widths thereof extending between opposite portions of side edges thereof, said resilient member having a length greater than its width and positioned separated from a portion of at least one of said side edges by more than said width of said resilient member; and engagement means adhered to said end surfaces and capable of engaging exposed surfaces of nasal outer wall tissues sufficiently to remain so engaged against said restoring forces, said truss includes deformable material between exposed surfaces of any nasal outer wall tissues engaged by said engagement means and said resilient member, *and* said truss and said engagement means [are] *being* capable of being manually released from exposed surfaces of any nasal outer wall tissues engaged by said engagement means.

26. The nasal dilator of claim [18] *23* wherein said truss and said engagement means together are formed as a strip having a length substantially greater than either of its width and thickness, and a width substantially greater than its thickness everywhere along said length.

29. The nasal dilator of claim [18] *23* wherein said restoring forces in said truss arising if said end surfaces are forced adjacent to one another by said spacing reduction forces are sufficient, upon removal of said spacing reduction forces, to restore most of said direct spacing present between said end surfaces before application of such spacing reduction forces.

31. The nasal dilator of claim [18] *23* wherein said spaced-apart end surfaces of said truss are terminated by end edges at opposite ends of said truss, and wherein said resilient member provides said restoring forces in said truss tending to restore said spacing between end surfaces thereof, said resilient member having opposite ends thereof each ending short of said end edges.

*33. The nasal dilator of claim 23 wherein a pair of spaced apart resilient members is secured in said truss.*

*34. The nasal dilator of claim 23 wherein said spaced apart end surfaces have an intermediate segment therebetween which is narrower in width than are said end surfaces.*

*35. A nasal dilator capable of introducing separating stresses in nasal outer wall tissues, comprising:*

*a truss of a single body with a resilient member and a flexible strip of material secured therein having a pair of spaced apart end surfaces which, if forced toward one another from initial positions to substantially reduce direct spacing therebetween by a spacing reduction force external to said truss, results in restoring forces in said truss tending to restore said direct spacing between said end surfaces; and*

*engagement means adhered to said end surfaces and capable of engaging exposed surfaces of nasal outer wall tissues sufficiently to remain so engaged against said restoring forces, said engagement means positioned at least in part between said resilient member and such nasal outer wall tissues when engaged therewith.*

*36. The nasal dilator of claim 35 wherein said end surfaces are limited in separation therebetween so that, when said end surfaces are engaging nasal outer wall tissues adjacent nasal passages, a surface of said truss can be in contact with nasal outer wall tissues for substantially all of that extent thereof between said end surfaces.*

*37. The nasal dilator of claim 35 wherein said truss includes deformable material between exposed surfaces of any outer nasal wall tissues engaged by said engagement means and said resilient member.*

*38. The nasal dilator of claim 37 wherein said flexible strip of material is located between said resilient member and said engagement means.*

*39. The nasal dilator of claim 35 wherein said truss and said engagement means are capable of being manually released from exposed surfaces of any nasal outer wall tissues engaged by said engagement means.*

*40. The nasal dilator of claim 35 wherein said truss and said engagement means together are formed as a strip having a length substantially greater than either its width and thickness, and a width substantially greater than its thickness everywhere along said length.*

*41. The nasal dilator of claim 35 wherein said single body of said truss is of plastic construction.*

*42. The nasal dilator of claim 35 wherein said spaced-apart end surfaces of said truss are terminated by end edges at opposite ends of said truss, and wherein said resilient member provides said restoring forces in said truss tending to restore said spacing between said end surfaces thereof, said resilient member having opposite ends thereof each ending short of said end edges.*

*43. The nasal dilator of claim 42 wherein said flexible strip of material is located between said resilient member and said engagement means.*

*44. The nasal dilator of claim 35 wherein said spaced apart end surfaces have an intermediate segment therebetween which is narrower in width than are said end surfaces.*

*45. The nasal dilator of claim 35 wherein said truss member has a pair of resilient members secured therein.*

*46. The nasal dilator of claim 45 wherein said resilient members are spaced apart from one another.*

*47. The nasal dilator of claim 46 wherein said pair of resilient members parallel one another at least in part.*

*48. The nasal dilator of claim 35 wherein said spaced apart end surfaces have a intermediate segment therebetween without its being engaged with said outer wall tissues adjacent thereto in contact therewith as are said end surfaces.*

49. A nasal dilator for preventing outer wall tissue of nasal passages of a nose from drawing in during breathing, comprising:

a unitary truss member having an initial state, the unitary truss member including:
a first end region adapted to engage the outer wall tissue of a first nasal passage;
a second end region adapted to engage the outer wall tissue of a second nasal passage;
an intermediate segment configured to traverse a portion of a nose located between the first and second nasal passages, the inherent tendency of the truss member to return to its initial state when flexed acting to stablize the outer wall tissue and thereby prevent the outer wall tissue of the first and second nasal passages from drawing in during breathing;
a flexible strip of material defining the first and second end regions and the intermediate segment; and
a resilient member secured to at least a tissue engaging portion of each of the first and second end regions, which tissue engaging portions are adapted to directly engage such outer wall tissue, and to a portion of the intermediate segment and to a first side of the flexible strip of material, the resilient member being capable, at least in part, of deformation that allows the truss member to conform to the outer wall tissue of the nasal passages of a nose and wherein the truss member includes an adhesive substance located on a second side of the flexible strip of material at the first and second end regions thereof for engaging, through releasably securing the truss member to, the outer wall tissue of the first and second nasal passages.

50. The nasal dilator of claim 49 wherein the intermediate segment between the end regions is narrower in width than are said end regions.

* * * * *